US005904928A

United States Patent [19]

Cyr et al.

[11] Patent Number: 5,904,928

[45] Date of Patent: May 18, 1999

[54] ANTITARTAR COMPOSITION AND ITS USE IN FOOD SUPPLEMENTS FOR ANIMALS

[75] Inventors: Jean-Paul Cyr, Beaumont; Jean-Marc Denoun, Paris, both of France

[73] Assignee: Societé à Responsabilité Limitee, Naintre, France

[21] Appl. No.: 08/844,704

[22] Filed: Apr. 18, 1997

[30] Foreign Application Priority Data

Apr. 19, 1996 [FR] France .................................. 96 04956

[51] Int. Cl.$^6$ .............................. A61K 7/16; A61K 7/18; A61K 7/28

[52] U.S. Cl. .......................... 424/442; 424/435; 424/439; 424/441; 424/49; 424/52; 424/54; 424/57; 424/50; 514/900; 514/902; 426/802; 426/805; 426/635; 426/648

[58] Field of Search ......................... 424/49–58; 426/805

[56] References Cited

U.S. PATENT DOCUMENTS

| | | | |
|---|---|---|---|
| 3,257,282 | 6/1966 | Muhler | 167/93 |
| 3,330,732 | 7/1967 | Muhler | 167/93 |
| 3,450,813 | 6/1969 | Muhler | 424/52 |
| 3,590,120 | 6/1971 | Muhler | 424/48 |
| 3,976,800 | 8/1976 | Deininger et al. | 426/311 |
| 4,145,447 | 3/1979 | Fisher et al. | 426/72 |
| 4,419,372 | 12/1983 | Greene et al. | 426/104 |
| 4,564,519 | 1/1986 | Pellico et al. | 424/48 |
| 4,822,626 | 4/1989 | Spanier et al. | 426/94 |
| 4,904,494 | 2/1990 | Spanier | 426/646 |
| 4,904,495 | 2/1990 | Spanier | 426/646 |
| 4,997,671 | 3/1991 | Spanier | 426/646 |
| 5,200,218 | 4/1993 | Easater et al. | 426/72 |
| 5,310,541 | 5/1994 | Montgomery | 424/50 |
| 5,336,494 | 8/1994 | Pellico | 424/94.4 |
| 5,405,836 | 4/1995 | Richar et al. | 514/23 |
| 5,607,681 | 3/1997 | Galloy et al. | 424/405 |
| 5,708,023 | 1/1998 | Mudak et al. | 514/494 |

FOREIGN PATENT DOCUMENTS

| | | |
|---|---|---|
| 0 173 568 A2 | 3/1986 | European Pat. Off. . |
| 0 277 383 A1 | 8/1988 | European Pat. Off. . |
| 0 366 869 A2 | 5/1990 | European Pat. Off. . |
| WO 93/11748 | 6/1993 | WIPO . |
| WO 94/05251 | 3/1994 | WIPO . |
| WO 94/08559 | 4/1994 | WIPO . |
| WO 95/21605 | 8/1995 | WIPO . |

OTHER PUBLICATIONS

Database WPI, Derwent Publications Ltd., AN 94–037343: XP002022212; HU–B–208 481 (Nov. 29, 1993).

*Primary Examiner*—Shep K. Rose
*Attorney, Agent, or Firm*—Darby&Darby

[57] ABSTRACT

The invention relates to an anti-tartar composition comprising:

(a) 0.5 to 5% by weight of at least one compound selected from among zirconium silicate and hydrated silica;

(b) 0.5 to 5% by weight of at least one compound selected from among chlorhexidine digluconate and zinc digluconate;

(c) 0.5 to 5% by weight of at least one compound selected from among potassium thiocyanate, glucose oxidase, lysozyme, and lactoperoxidase; and (d) 1 to 5% by weight of at least one acid compound selected from among vitamin C and citric acid.

It also concerns the use thereof in combination with food supplements or chewable supports for animals as well as the food supplements and chewable articles thus obtained.

The invention applies, in particular, to the control of the formation of tartar in domestic animals such as dogs.

4 Claims, No Drawings

ANTITARTAR COMPOSITION AND ITS USE IN FOOD SUPPLEMENTS FOR ANIMALS

FIELD OF THE INVENTION

The present invention lies within the field of the control of tartar, in particular in domestic animals such as dogs.

BACKGROUND OF THE INVENTION

More particularly, the invention relates to an anti-tartar composition, which makes it possible to combat the formation of tartar, as well as to its use in combination with a food supplement or a chewable article for animals.

The present invention lies within the field of the control of tartar, in particular in domestic animals such as dogs.

More particularly, the invention relates to an anti-tartar composition, which makes it possible to combat the formation of tartar, as well as to its use in combination with a food supplement or a chewable article for animals.

The invention also relates to food supplements and chewable articles for animals, which have an anti-tartar action.

The formation of tartar, in particular in dogs, can favor the development of periodontitis with consequences in particular on the quality and condition of the enamel and/or the gums or else at the cardiovascular level.

In order to combat tartar and its deleterious effects in domestic animals, their owners frequently call upon the veterinarian.

In parallel, when it is desired to avoid or limit this type of consultation, tablets having an anti-tartar action are known.

However, dogs frequently swallow these tablets as soon as they are given to them. Therefore, they do not chew them or keep them sufficiently long in their mouth in order to achieve an acceptable effectiveness.

This may furthermore lead to a large and excessive consumption of these tablets, without being able to obtain the desired effect or, at least, without being able to obtain such effect in a satisfactory manner.

Other forms can be contemplated such as, for instance, dentifrices.

However, from a practical standpoint, that type of product is difficult to use in animals and requires the intervention of the owner, who may be somewhat squeamish, or else recourse to a specialized dog grooming service.

Chewable objects for dogs are also known which, by the chewing of them, have an abrasive action due to the flow of saliva, which may prevent the tartar from depositing in excessively large amount.

Nevertheless, the effectiveness of these chewable articles is limited and they do not make it possible satisfactorily to destroy tartar, which has already formed.

Thus, it would appear necessary to find new agents for combating tartar and its harmful effects, in animals and in particular dogs, which agents would make it possible to prevent, or at least limit, the development of diseases, which may be related thereto, in particular the development of periodontitis.

Furthermore, this need would seem to be becoming more and more important, inasmuch as the number of pets is continuing ceasing to increase, particularly dogs.

SUMMARY OF THE INVENTION

Thus, the object of the present invention is to provide an anti-tartar composition, which makes it possible to combat tartar effectively.

Another object is to provide food supplements or other particularly effective chewable anti-tartar articles, the form of which does not present the drawbacks indicated above and which can be used for pets simply and effectively.

Another object is to provide such supplements and chewable articles, which do not require extensive and difficult intervention on the part of the owner.

More particularly, the invention relates to food supplements and chewable articles intended for dogs.

For this purpose, the present invention has as its object an anti-tartar composition, which is characterized by the fact that it comprises:

- 0.5 to 5% by weight of at least one compound selected from among zirconium silicate and hydrated silica;
- 0.5 to 5% by weight of at least one compound selected from among chlorhexidine digluconate and zinc digluconate;
- 0.5 to 5% by weight of at least one compound selected from among potassium thiocyanate, glucose oxidase, lysozyme and lactoperoxidase;
- 1 to 5% by weight of at least one acid compound selected from among vitamin C and citric acid.

Another object of the invention is the use of said composition in anti-tartar food supplements for animals.

Still another object is animal anti-tartar food supplements, which contain the said composition.

A further object is the use of said composition in combination with chewable supports.

Still another object is a chewable anti-tartar article for domestic animals containing said composition.

An object of the present invention is an anti-tartar composition intended to control tartar, particularly in domestic animals.

DETAILED DESCRIPTION OF THE INVENTION

In accordance with the invention, the expression "to control tartar" means not only to avoid or limit the formation of tartar but also to destroy tartar, which has already formed.

The percentages are expressed as percentages by weight, referred to the total weight of the composition.

The composition in accordance with the invention may comprise one or more other supplementary ingredients such as fluorine derivatives.

The fluorine derivative or derivatives are preferably selected from among sodium monofluorophosphate and sodium fluoride. The composition preferably comprises 0.2 to 5% by weight of sodium monofluorophosphate and 0.05 to 1% by weight of sodium fluoride.

One preferred composition in accordance with the invention is:

- 0.5 to 5% by weight of zirconium silicate;
- 0.5 to 5% by weight of chlorhexidine digluconate;
- 0.5 to 5% by weight of potassium thiocyanate;
- 1 to 5% by weight of vitamin C;
- 1 to 5% by weight of citric acid;
- 0.2 to 5% by weight of sodium monofluorophosphate;
- 0.05 to 1% by weight of sodium fluoride.

The composition in accordance with the invention makes it possible, in parallel with its action on tartar, to combat bad breath.

The composition defined above can be prepared by any known process. In particular, the different aforementioned components can be mixed in the water, the feed, or any other binder.

In accordance with another feature of the invention, the anti-tartar composition is advantageously used in combination with a chewable support.

By "chewable support" there is understood a support, which involves a certain amount of mastication, favoring the flow of saliva, and which results in a dwell time in the mouth of the animal, which is sufficient to permit effective action of the anti-tartar composition of the invention.

There is preferably selected a support, which has a certain abrasive character, which can combine with the action of the anti-tartar composition.

Of course, the size and shape of the chewable support for the anti-tartar composition of the present invention are modified depending on the type of animal, which is to be treated.

In accordance with one preferred embodiment of the invention, the composition is associated with a food supplement.

This food supplement advantageously has a certain chewable character, which combines with the effect of the composition, which has been previously described in order to give a particularly satisfactory result.

The food supplement may, in particular, consist of a dog bone.

This dog bone is formed from a base of proteins and vitamins and is completely digestible. It is dry and has a certain hardness, as well as an abrasive character. This type of bone encourages mastication by the dog.

In order to obtain the food supplement, the anti-tartar composition is incorporated in the basic ingredients upon the manufacture of the dog bone.

Furthermore, due to its shape, the bone cannot be directly bitten apart or swallowed. Thus, when the bone is given to the dog, the dog is forced to gnaw it, which further improves the anti-tartar effect of the food supplement.

The food supplement may constitute a treat or delicacy for the dog.

The composition of the invention combined with such a dog bone makes it possible both to avoid the formation of tartar and to destroy tartar, which has already formed.

The intervention of the owner is furthermore very limited, since it is merely necessary to give the anti-tartar dog bone to the dog.

The composition in accordance with the present invention can also be combined with some other type of chewable support, such as, for instance, buffalo skin and toys, particularly plastic toys.

These articles can be impregnated or coated with a composition in accordance with the invention upon their preparation or at the end thereof, as the case may be.

In accordance with the present invention, the amount of food supplement or of chewable anti-tartar articles given to the animal is adapted to amount of tartar, from which the animal suffers.

The treatment with food supplements or other articles of anti-tartar effect in accordance with the invention can be carried out in order to prevent the formation of tartar or in order to destroy tartar, which has already formed, depending on the amount of tartar developed by the animal in question.

This treatment may also be supplemented by a conventional mechanical removal of tartar effected by a veterinarian in order to prolong the effects thereof.

It can also be advantageously used when descaling is not recommended by the veterinarian due to the condition of health or the age of the animal.

The invention will now be described in further detail on the basis of the following example, which is given by way of illustration and not of limitation.

EXAMPLE

The following anti-tartar composition is prepared:

1% by weight by weight of zirconium silicate;

1% by weight of chlorhexidine digluconate;

1% by weight of potassium thiocyanate;

1.5% by weight of vitamin C;

1.5% by weight of citric acid;

0.76% by weight of sodium monofluorophosphate;

0.10% by weight of sodium fluoride.

This composition is combined with the following food-bone composition;

32.56% by weight of casein;

32.56% by weight of poultry meal;

3.725% of gelatin.

The different components are mixed in the presence of water. The proportion of anti-tartar composition is about 7% by weight referred to the total weight of the mixture.

Study On The Action On The Condition Of Tartration And/Or On The Prevention Of The Appearance Of Tartar On the basis of this example there are prepared anti-tartar dog bones of different sizes in accordance with the dogs, for which they are intended, namely 40 gram bones for "small dogs" and 70 gram bones for "large dogs".

The bones previously prepared were tested on 42 dogs selected from among the following breeds:

| | | | |
|---|---|---|---|
| I. | Fox terrier | X. | Mixed-breed basset |
| II. | German shepherd | XI. | Beaucaron |
| III. | Nizinny | XII. | Standard poodle |
| IV. | Cocker spaniel | XIII. | Pinscher |
| V. | Tibet terrier | XIV. | Toy poodle |
| VI. | Westie | XV. | Dachshund |
| VII. | Miniature poodle | XVI. | Whippet |
| VIII. | Collie | XVII. | Briard |
| IX. | Yorkie | | |

For this study, the following four stages of tartar development (Stages 1 to 4) are considered, starting from a condition considered normal (Stage 0):

Stages of Tartar Development

| STAGE | TARTAR DEVELOPMENT |
|---|---|
| 4 | 100% |
| 3 | 75% |
| 2 | 50% |
| 1 | 25% |
| 0 | No tartar |

The number of bones given to each dog is 8 bones per month per dog.

The dogs are examined twice a month for three months.

The examination concerns the condition of the gums and of the dental plaque as well as the stage of tartar development.

The results are set forth in Tables I and II below:

TABLE I

STAGES OF TARTAR DEVELOPMENT

| | No. of | STAGES OF TARTAR DEVELOPMENT | | | | |
|---|---|---|---|---|---|---|
| | Dogs | 4 | 3 | 2 | 1 | 0 |
| Initial Examination | 42 | 28 | 7 | 2 | 3 | 2 |
| + 15 days | 42 | 22 | 9 | 4 | 4 | 3 |
| + 30 days | 42 | 18 | 7 | 6 | 6 | 5 |
| + 45 days | 42 | 11 | 8 | 3 | 12 | 8 |
| + 60 days | 42 | 7 | 11 | 5 | 10 | 9 |
| + 75 days | 42 | 4 | 3 | 4 | 15 | 16 |
| + 90 days | 42 | 1 | 0 | 3 | 12 | 26 |

TABLE II

PERCENTAGE IMPROVEMENT IN THE STAGE OF TARTAR DEVELOPMENT

| STAGE | INITIAL EXAMINATION | END OF TEST |
|---|---|---|
| 4 | 66.66% | 2.38% |
| 3 | 16.66% | 0% |
| 2 | 4.76% | 7.14% |
| 1 | 7.14% | 28.57% |
| 0 | 4.76% | 61.90% |

Good partiality for the bone was noted without extensive digestive disorders.

These results show, in particular, that when the bone is ingested regularly at a rate of 8 bones a months for the period "of attack" of three months, a significant decrease in the stage of tartar development is obtained.

Faster improvements were noted in dogs passing from stage 4 to stages 2 or 1 more suddenly than others.

A single animal remained in stage 4 due to the poor condition of its dentition (loosened teeth).

The number of bones may be 2 per week in the first month, 1 a week in the second month, and 2 a month in the third month, etc.

However, the number of bones must be selected on the basis of the animals.

A definite improvement in the breath was also observed as from the consumption of the first bones.

We claim:

1. A food dog bone composition comprised of: (A) 93% of 32.56% by weight of casein; 32.56% by weight of poultry meal; 3,725% by weight of gelatin, and, 7% of (B) an anti-tartar composition comprised of: in parts by weight, 1% zirconium silicate;

1% chlorhexidine digluconate;

1% potassium thiocyanate;

1.5% vitamin C;

1.5% citric acid;

0.76% sodium monofluorophosphate; and 0.10% sodium fluoride.

2. A method for removing tartar from the teeth of an animal comprising administering the composition of claim 1, in a chewable support.

3. The method of claim 2, wherein the chewable support is a dog bone.

4. The method of claim 2, wherein said animal is a dog.

* * * * *